United States Patent
Pusterla et al.

(10) Patent No.: US 7,323,344 B2
(45) Date of Patent: Jan. 29, 2008

(54) METHOD OF MEASURING THE CONCENTRATION OF HYDROGEN AND METHANE IN NITROGEN BY ION MOBILITY SPECTROMETRY

(75) Inventors: Luca Pusterla, Milan (IT); Marco Succi, Milan (IT)

(73) Assignee: Saes Getters S.p.A., Lainate (Milan) (IT)

( * ) Notice: Subject to any disclaimer, the term of this patent is extended or adjusted under 35 U.S.C. 154(b) by 988 days.

(21) Appl. No.: 10/702,904

(22) Filed: Nov. 6, 2003

(65) Prior Publication Data

US 2004/0094701 A1 May 20, 2004

Related U.S. Application Data

(63) Continuation of application No. PCT/IT02/00262, filed on Apr. 23, 2002.

(30) Foreign Application Priority Data

May 7, 2001 (IT) .......................... MI2001A0930

(51) Int. Cl.
- G01N 33/22 (2006.01)
- G01N 1/18 (2006.01)
- G01N 1/22 (2006.01)
- H01J 49/04 (2006.01)
- H01J 49/40 (2006.01)

(52) U.S. Cl. ...................... 436/144; 250/281; 250/282; 250/286; 250/287; 250/288; 436/139; 436/141; 436/173; 436/175; 436/178; 436/181

(58) Field of Classification Search ........ 250/281–283, 250/286–288; 436/43, 139, 141, 144, 173–175, 436/177–178, 181
See application file for complete search history.

(56) References Cited

U.S. PATENT DOCUMENTS

| 4,306,887 A | 12/1981 | Barosi et al. |
| 4,317,995 A * | 3/1982 | Bradshaw et al. .......... 250/288 |
| 4,378,499 A | 3/1983 | Spangler et al. |

(Continued)

FOREIGN PATENT DOCUMENTS

EP      0 902 283 A1    3/1999

(Continued)

OTHER PUBLICATIONS

Dotan, I. et al, Journal of Chemical Physics 1976, 65, 5028-5030.*

(Continued)

*Primary Examiner*—Arlen Soderquist
(74) *Attorney, Agent, or Firm*—Akin Gump Strauss Hauer & Feld LLP

(57) ABSTRACT

A method is provided for the quantitative analysis of the contents, in nitrogen, of hydrogen and methane by ionic mobility spectrometry. The method includes the steps of: a) performing a measurement of the apparent hydrogen concentration in the nitrogen to be analyzed; b) performing a measurement of the apparent hydrogen concentration in a flow of the same sample of nitrogen, purified of all impurities but methane; and c) comparing the two measurements. A system of branched lines is also provided for carrying out the method.

10 Claims, 2 Drawing Sheets

U.S. PATENT DOCUMENTS

| | | | |
|---|---|---|---|
| 5,283,199 A | | 2/1994 | Bacon, Jr. et al. |
| 5,304,796 A | | 4/1994 | Siefering et al. |
| 5,457,316 A | | 10/1995 | Cohen et al. |
| 5,475,217 A | * | 12/1995 | Bradshaw .................. 250/287 |
| 5,723,861 A | * | 3/1998 | Carnahan et al. ........... 250/287 |
| 5,736,739 A | * | 4/1998 | Uber et al. .................. 250/287 |
| 5,955,886 A | | 9/1999 | Cohen et al. |
| 6,639,214 B1 | * | 10/2003 | Ketkar et al. ............... 250/287 |

FOREIGN PATENT DOCUMENTS

| | | |
|---|---|---|
| GB | 2 177 080 A | 1/1987 |
| WO | WO 02-052255 A1 | 7/2002 |

OTHER PUBLICATIONS

Ogino, H. et al, Analytical Chemistry 1991, 63), 1376-1379.*

Ridgeway, R. G. et al, Proceedings—Institute of Environmental Sciences 1992, 38th, 68-73.*

Siefering, K. et al, Proceedings—Institute of Environmental Sciences 1992, 38th, 74-81.*

Ketkar, S. N. et al, Journal of the Electrochemical Society 1992, 139, 3675-3678.*

Kimura, T. et al, Proceedings—Institute of Environmental Sciences 1993, 39TH, 14-19.*

Mitsui, Y. et al, Japanese Journal of Applied Physics, Part 1 1993, 32, 2886-2891.*

Siefering, K. et al, Journal of Vacuum Science & Technology, A 1993, 11, 1593-1597.*

Solcia, C. et al, Proceedings—Institute of Environmental Sciences 1994, 40th, 53-61.*

Stimac, R. M.et al, Proceedings—Institute of Environmental Sciences 1996, 42nd, 5-12.*

Pusterla, L. et al, Proceedings—Institute of Environmental Sciences 1997, 43rd, 336-346.*

Ketkar, S. N. et al, Analytical Chemistry 2001, 73, 2554-2557.*

Baumbach et al., "Ion Mobility Spectrometry: Arriving On Site and Moving Beyond a Low Profile", *Applied Spectroscopy*, vol. 53, No. 9, pp. 338A-355A, 1999.

Backx et al., "Electron-ion coincidence measurements of $CH_4$", *J. Phys. B: Atom. Molec. Phys.*, vol. 8, No. 18, pp. 3020-3033, 1975.

* cited by examiner

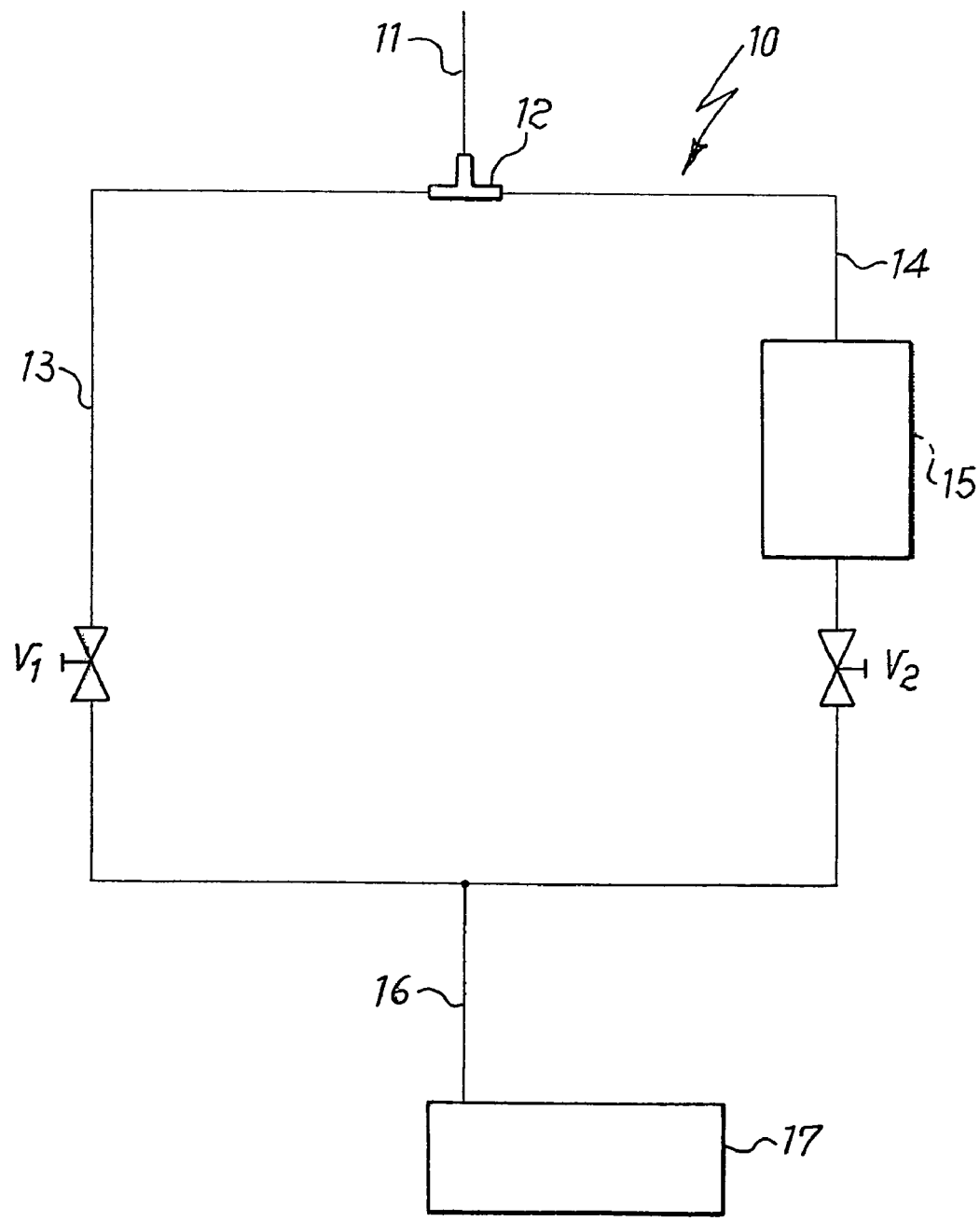

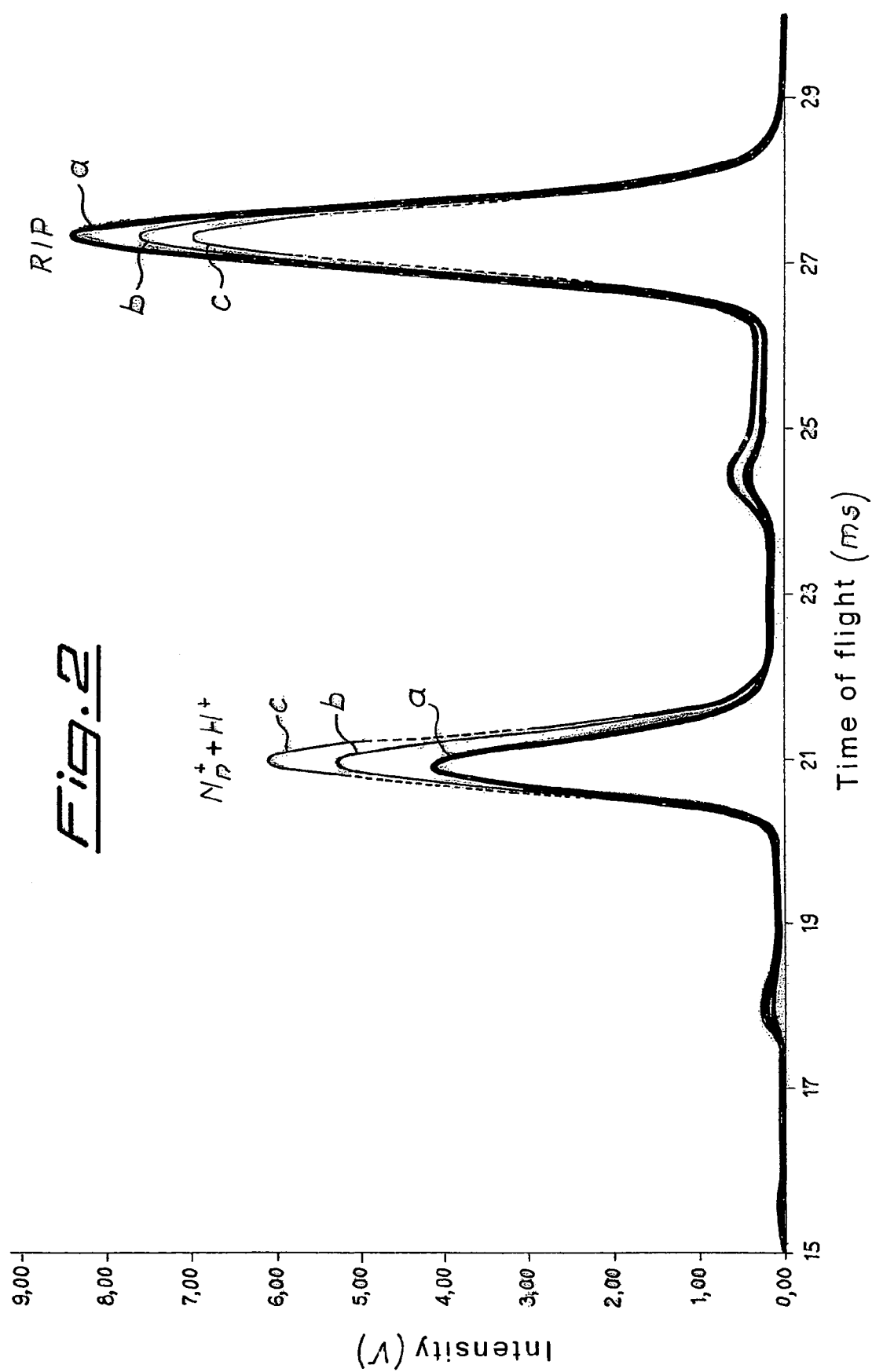

METHOD OF MEASURING THE CONCENTRATION OF HYDROGEN AND METHANE IN NITROGEN BY ION MOBILITY SPECTROMETRY

CROSS-REFERENCE TO RELATED APPLICATIONS

This application is a continuation of International Application No. PCT/IT02/00262, filed Apr. 23, 2002, which was published in the English language on Nov. 14, 2002, under International Publication No. WO 02/090960 A2.

BACKGROUND OF THE INVENTION

The present invention relates to a method of measuring the concentration of hydrogen and methane in nitrogen by ion mobility spectrometry.

Nitrogen is widely employed as a reacting medium or carrier gas in the integrated circuit industry. As is known, in the manufacture of these devices, the purity of all the used materials has a basic importance. As a matter of fact, contaminants possibly present in the reactants or in the reaction environment may be incorporated into the solid state devices, thus altering their electrical features and giving rise to production wastes. The purity specifications of the gases employed in production may change among different manufacturers and depending on the specific process the gas is employed in. Generally, a gas is considered to be acceptable for manufacturing purposes when its impurities content does not exceed 10 ppb (parts per billion, namely an impurity molecule per $10^9$ total gas molecules). Preferably, the impurities content is lower than 1 ppb. It thus becomes important to have the possibility to measure extremely low concentrations of impurities in the gases in an accurate and reproducible way.

A technique that can be exploited for such purpose is ion mobility spectrometry, which is also known in the art under the abbreviation IMS. The same abbreviation is also used for the instrument employed to perform this technique, while indicating, in this case, "Ion Mobility Spectrometer". The interest in such a technique comes from its extremely high sensitivity, associated with limited size and cost of the instrument. By operating in suitable conditions, it is possible to detect gas or vapor phase species, in a gas medium, in amounts of the picogram order (pg, namely $10^{-12}$ g) or in concentrations of the order of parts per trillion (ppt, equivalent to one molecule of analyzed substance per $10^{-12}$ molecules of sample gas). IMS instruments and analytical methods in which they are employed are disclosed, for instance, in U.S. Pat. Nos. 5,457,316 and 5,955,886, assigned to the US company PCP Inc.

The physicochemical grounds of the technique are very complicated, just as the interpretation of the IMS analytical results. For an explanation of these grounds and results, reference can be made to the book *Ion Mobility Spectrometry* by G. A. Eiceman and Z. Karpas, published in 1994 by CRC Press.

Briefly, an IMS instrument essentially consists of a reaction zone, a separation zone and a collector of charged particles.

Within the reaction zone takes place the ionization of the sample, comprising gases or vapors to be analyzed in a carrier gas, usually by means of β-radiation emitted by $^{63}Ni$. The ionization mainly occurs on the carrier gas, with the formation of the so-called "reactant ions," whose charge is then distributed to the present species depending on their electron or proton affinities or on their ionization potentials.

The reaction zone is divided from the separation zone by means of a grid which, when maintained at a suitable potential, prevents the ions produced in the reaction zone from entering into the separation zone. The analysis "time zero" is established by the moment when the grid potential is annulled, thus allowing the ions admission into the separation zone.

The separation zone comprises a series of electrodes which create such an electric field that the ions are carried from the grid towards the collector. In this zone, maintained at atmospheric pressure, a gas flow is present having an opposite direction with respect to that of the ions' movement. The counterflow gas (defined in the field as "drift gas") is an extremely pure gas, that may either correspond to the gas whose impurities content is to be determined, or may be a different gas. For instance, for determining the impurities content in nitrogen it is either possible to use a counterflow of pure nitrogen or argon, as disclosed for instance in Italian patent application MI2000-A-002830, assigned to SAES Getters, S.p.A. The motion velocity of the ions depends on the electric field and on the cross-section of the same ions in the gaseous medium, so that different ions take different times for crossing the separation zone and reaching the particles collector. The time elapsed from "time zero" to the time of arrival on the particle collector is called "time of flight." The collector is connected to the signal processing system, which transforms the current values sensed as a function of time in the final graph, where peaks corresponding to the different ions are shown as a function of the "time of flight." From the determination of this time and the knowledge of the test conditions, it is possible to trace the presence of the substances, which are the object of the analysis, whereas from the peaks' area it is possible to calculate, through suitable computation algorithms, the concentration of the corresponding species.

In order to get good results from such a type of analysis, it is necessary that the peaks corresponding to the various species be well distinct and separated from one another. In a few cases, however, this condition is not satisfied. That is what happens, for example, in the case of the analysis of methane as an impurity in nitrogen. Within the reaction zone methane dissociates into $H^+$ ions and $CH_3^-$ radicals (these latter are not "visible" in the IMS analysis as being neutral species). As a consequence, it is impossible to measure methane whose hydrogen concentration is higher than that actually present in nitrogen at the instrument's inlet.

BRIEF SUMMARY OF THE INVENTION

An object of the present invention is to provide a method of measuring the concentration of hydrogen and methane in nitrogen by ion mobility spectrometry.

According to the present invention, such an object is achieved through a method comprising the following steps:

a) carrying out a measurement of the apparent hydrogen concentration in the untreated nitrogen to be analyzed;

b) carrying out a measurement of the apparent hydrogen concentration in a flow of the nitrogen to be analyzed, purified from every kind of impurity but methane, thus indirectly deducing the real methane concentration; and c) subtracting the hydrogen concentration measured in step b) from the hydrogen concentration measured in step a), thus deducing the real hydrogen concentration in the nitrogen to be analyzed.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings:

FIG. 1 is a schematic diagram of a system of gas lines comprising a purifier for the practical realization of the method of the invention; and FIG. 2 is a graphical representation showing the results of three different IMS analyses of nitrogen, in one case of pure nitrogen and in two cases of nitrogen with impurities.

DETAILED DESCRIPTION OF THE INVENTION

As previously stated, the details concerning the charge transfer mechanisms occurring in an IMS analysis are extremely complicated. It was, however, found that nitrogen transfers charge to methane with an efficiency which is about double that of the charge transfer to hydrogen. Methane then dissociates according to the following reaction equation:

$$CH_4^+ \rightarrow CH_3\cdot + H^+ \quad (I)$$

wherein $CH_3\cdot$ stands for the neutral methyl radical.

As a consequence of the higher charge transfer efficiency to methane, and of reaction (I), the final effect on the IMS analysis result is that the methane contribution to the hydrogen peak is higher than that of hydrogen itself. The precise value of the transfer efficiency ratio to methane and hydrogen (which is nearly 2, as previously stated) varies depending on the analysis conditions (temperature, gas flows, etc.) and can be determined from time to time in the particular conditions by calibration tests at different methane concentrations. In the following, the hydrogen concentration measured in the IMS analysis stemming from hydrogen originally present in nitrogen and from methane will be indicated by $H_H$ and $H_{CH4}$, respectively.

When an impurities analysis in nitrogen is carried out, the resulting hydrogen concentration measure, as stated already, is an apparent concentration, indicated in the following by $H_{APP}$, due to $H_H$ and $H_{CH4}$ contributions, which does not enable the precise quantification of either the hydrogen or the methane concentration.

According to the method of the invention, then, in operation a) the measurement of $H_{APP}$ is performed; in operation b) the measurement of $H_{CH4}$ is performed, thus obtaining an indirect measure (through measurement of hydrogen concentration) of the actual methane concentration in the nitrogen to be analyzed; and in operation c) the contribution of hydrogen stemming from methane is subtracted from the $H_{APP}$ measurement, thus achieving the measurement of hydrogen really present in nitrogen. The evaluation of $H_{APP}$, $H_H$ and $H_{CH4}$ measurements, as well as the calculation of the difference as per step c) of the method of the invention, will generally be realized in an automated way through a data processing system, generally a microprocessor, connected to the instrument.

The method of the invention may be put into practice exploiting the gas lines system schematically shown in FIG. 1. System 10 consists of an inlet line 11 for the gas under examination. Line 11 is subdivided, through a branching element 12, into secondary lines 13 and 14, respectively provided with on-off valves $V_1$ and $V_2$. On line 14 there is also arranged a gas purification system 15, able to remove from inlet nitrogen all impurities but methane. Lines 13 and 14 are reconnected, downstream of the valves and of the purifier, as a unified line 16, feeding the gas outgoing from the system to an IMS instrument 17, and in particular to the reaction zone (not shown) of the instrument. A few modifications are possible of the system of FIG. 1: for instance, lines 13 and 14 could be not reconnected as a unified line 16, but they could be directly connected to the reaction zone of the IMS instrument. In this respect, however, the system of FIG. 1 has an advantage as it does not need a modification of the commercially available IMS instruments, which are generally provided with only one inlet point for the gas to be analyzed. Moreover, valve $V_2$ may lie upstream of the purification system 15. Finally, system 15 may consist of a single purifier or of several purifiers in series.

Suitable nitrogen purifiers for the purposes of the invention are known and available on the market. For instance, system 15 may comprise a purifier based on the use of a getter alloy, having the weight percent composition Zr 76.5%-Fe 23.5% manufactured and sold by SAES Getters S.p.A. under the trademark St 198. This alloy and its production are disclosed in U.S. Pat. No. 4,306,887. Use of alloy St 198 for nitrogen purification is disclosed in British patent GB-B-2,177,080. This alloy, employed at temperatures of about 300° C., is able to completely remove impurities like hydrogen, oxygen, water and carbon oxides, without adsorbing, however, nitrogen and methane. This alloy is therefore suited to the purposes of the invention, as it neither adsorbs nitrogen (which, if absorbed, would rapidly saturate the alloy's capacity, as it represents the main gas) nor the critical impurity, methane, which would not allow the method to be carried out if it were absorbed in an even minimal amount.

Another material especially suited to the purposes of the invention is metallic nickel, generally used on a high surface area carrier, for instance molecular sieves. Metallic nickel too, when used at room temperature, is able to remove the impurities commonly present in nitrogen except for methane. Supported metallic nickel, or purifiers containing the same, are commercially available for instance from the US company Engelhard Co.

It is possible to combine, with these purifiers, other gas purifiers known in the art, for instance the ones based on molecular sieves for water sorption.

By using the system of FIG. 1, keeping valve $V_1$ opened and closing valve $V_2$, untreated nitrogen to be analyzed is supplied to the IMS instrument. Under these conditions, there are present both methane, giving rise to reaction (I), and the hydrogen initially present in nitrogen. By performing the IMS analysis under these conditions, one reads hydrogen concentration $H_{APP}$, thus carrying out the step a) of the method according to the invention.

Operation b), on the contrary, is carried out by closing valve $V_1$ and opening valve $V_2$. All the flow goes through purification system 15, which removes all impurities present in nitrogen but methane. Under these conditions, the IMS measure will read hydrogen concentration $H_{CH4}$, thus allowing to indirect deduction of the concentration of methane alone in the nitrogen to be analyzed.

Finally, operation c) is developed by the data processing system connected to the instrument.

The invention will be further illustrated by the following examples.

Test results are given on graphs where peaks are recorded as a function of their time of flight in milliseconds (ms). Peaks have an area corresponding to the concentration of the different ions. These ions are generally complex species, which may comprise one, two or more molecules of the ionized gas, possibly associated to more than one molecule of carrier gas. For sake of simplicity, the main peaks in the graphs are identified by the formula of the molecular species they are ascribed to, rather than by the formula of the corresponding ion. The peak intensity is given in volts (V). The transformation of the current directly measured by the sensor (number of ions colliding onto the sensor per time unit) into volts is performed by the instrument electronics. The sample ionization is performed by a radioactive source of $^{63}$Ni. The separation zone of the employed instrument is 8 cm long. In all of the tests, the applied electric field is equal to 128 V/cm. Gases employed in the tests are supplied by the firm SIAD (Bergamo, Italy), in cylinders containing pure nitrogen or mixtures of nitrogen and of 20 ppm of the concerned impurity, which can be either hydrogen or methane.

EXAMPLE 1

This example is representative of an impurities analysis on nitrogen according to the method of the invention.

First of all, an IMS analysis of pure nitrogen is carried out, in order to track the background spectrum of the system that will be used as a reference item in the following tests. The test is carried out at 110° C., while using pure argon as a drift gas and a 0.15 flow ratio between the sample gas and the drift gas. The result of this test is recorded in FIG. 2 as line a. The peak occurring in correspondence of a time of flight of about 27 ms is the peak of the main ion present, containing the species $N_2^+$. This ion, corresponding to the gas showing the highest concentration in the analysis, whose impurities concentration has to be determined, is defined in the art as reactant ion peak, abbreviated as RIP. The peak centered at 21 ms corresponds to species containing an odd number of nitrogen atoms, such as $N_3^+$, $N_5^+$ and so on, indicated in FIG. 2 as $N_n^+$.

EXAMPLE 2

A test is then carried out according to operation b) of the method of the invention. A nitrogen flow, containing 20 ppm of methane, is diluted with pure nitrogen to a 2 ppb concentration of methane. The use of nitrogen exclusively containing methane is equivalent to the gas purification obtainable from system 10 by closing valve $V_1$ and opening valve $V_2$. This gas flow is sent to the analyzer. A spectrum is obtained which is recorded on FIG. 2 as line b. Hydrogen peak falls at 21 ms, namely at the same time as the species derived from nitrogen, but it is possible to deduce the contribution of hydrogen alone by subtracting the areas. Because of this overlapping, the peak on the Fig. is indicated as $N_n^+ + H^+$. The $H_{CH4}$ value, corresponding to 2 ppb, is deduced from line b by the instrument's processing system, which takes into account the correction factor for the higher charge transfer efficiency from nitrogen to methane with respect to hydrogen.

EXAMPLE 3 (COMPARATIVE)

Finally, a comparison test is carried out, corresponding to the known procedure of performing an impurities analysis in nitrogen.

A nitrogen flow, containing 20 ppm of hydrogen and a nitrogen flow containing 20 ppm of methane are mixed and diluted with pure nitrogen to a 2 ppb concentration of both impurities. This gas is directly sent to the IMS instrument. The test results are recorded on a graph in FIG. 2 as line c. A hydrogen concentration value of 6 ppb is deduced from this line by means of the instrument's processing system, by subtracting the contribution of the nitrogen background from the peak at 21 ms.

The test of Example 3 corresponds to the known performing procedure of the impurities analysis in nitrogen. As has been seen, this analysis gives a cumulative measure of the impurities hydrogen and methane, which is however impossible to subdivide into the respective contributions deriving from hydrogen and methane. Furthermore, the hydrogen reading obtained in this way (6 ppb) is higher than the one which should be obtained (4 ppb), due to the 2 ppb of hydrogen and the 2 ppb of methane. By this method, it is thus impossible to quantitatively determine hydrogen and methane in nitrogen.

Through the method of the invention (Example 2), on the contrary, it is possible to isolate the contribution of the $H_{CH4}$ value to the $H_{APP}$ value. The precise $CH_4$ concentration is deduced from the $H_{CH4}$ reading after calibration of the instrument. From the knowledge of this concentration and from the measurement of $H_{APP}$ it is then possible to correctly deduce the hydrogen concentration initially present in nitrogen.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of measuring concentrations of hydrogen and methane in nitrogen by ion mobility spectrometry, comprising the following steps:
   a) carrying out a measurement of apparent hydrogen concentration ($H_{APP}$) in untreated nitrogen to be analyzed;
   b) carrying out a measurement of a concentration of hydrogen stemming from methane ($H_{CH4}$) in a flow of the nitrogen to be analyzed, purified from all impurities but methane, thus indirectly deducing a real methane concentration; and
   c) subtracting the hydrogen concentration measured in operation b) from the hydrogen concentration measured in operation a), thus performing the operation $H_{APP} - H_{CH4}$ to obtain as a result of the subtraction a value ($H_H$) being a real hydrogen concentration in the nitrogen to be analyzed.

2. The method according to claim 1, wherein the concentration measurements and the subtraction operation are performed in an automated way through a data processing system.

3. The method according to claim 2, wherein the data processing system is a microprocessor.

4. The method according to claim 1, wherein operation a) is carried out by directly sending to an IMS instrument the nitrogen to be analyzed, and operation b) is carried out on nitrogen previously made to flow through a purification system able to remove all impurities but methane from the nitrogen.

5. The method according to claim 4, wherein a system (10) of gas lines is used, which comprises an inlet line (11)

for the nitrogen under examination; the inlet line being subdivided, through a branching element (12), into two secondary lines (13; 14); wherein on each secondary line there is an on-off valve ($V_1$; $V_2$) and on only one of the lines (14) there is also arranged a nitrogen purification system (15); the secondary lines being connected, downstream of the valves and the purifying system, to a reaction zone of the IMS instrument (17).

6. The method according to claim 5, wherein operation a) is carried out by sending the nitrogen to be analyzed into the system of gas lines, while keeping open the valve on the secondary line where the purification system is not present and keeping closed the valve on the line where the purification system is present; and wherein operation b) is carried out by sending the nitrogen to be analyzed into the system of gas lines, while keeping closed the valve on the line where the purification system is not present and keeping open the valve on the line where the purification system is present.

7. The method according to claim 5, wherein the purification system comprises a single purifier.

8. The method according to claim 7, wherein the purifier contains an alloy having a weight percent composition Zr 76.5%-Fe 23.5%.

9. The method according to claim 7, wherein the purifier contains metallic nickel on a carrier having a high surface area.

10. The method according to claim 5, wherein the purification system comprises at least two purifiers, one of which is intended for water sorption and is based on molecular sieves.

* * * * *